United States Patent
Ohashi et al.

(10) Patent No.: US 11,366,089 B2
(45) Date of Patent: Jun. 21, 2022

(54) ANALYSIS CONDITION ADJUSTING DEVICE OF SIMPLE FUEL ANALYZER

(71) Applicant: MITSUBISHI HEAVY INDUSTRIES, LTD., Tokyo (JP)

(72) Inventors: Ryohei Ohashi, Tokyo (JP); Toshihiko Setoguchi, Tokyo (JP); Junji Imada, Tokyo (JP); Atsushi Tanaka, Tokyo (JP); Keigo Matsumoto, Tokyo (JP)

(73) Assignee: MITSUBISHI HEAVY INDUSTRIES, LTD., Tokyo (JP)

(*) Notice: Subject to any disclaimer, the term of this patent is extended or adjusted under 35 U.S.C. 154(b) by 799 days.

(21) Appl. No.: 16/275,877

(22) Filed: Feb. 14, 2019

(65) Prior Publication Data

US 2019/0285601 A1 Sep. 19, 2019

(30) Foreign Application Priority Data

Mar. 14, 2018 (JP) .............................. JP2018-046789
Apr. 23, 2018 (JP) .............................. JP2018-082219

(51) Int. Cl.
  *G01N 33/00* (2006.01)
  *F22B 35/00* (2006.01)
  *G01N 33/22* (2006.01)

(52) U.S. Cl.
  CPC ........ *G01N 33/0073* (2013.01); *G01N 33/007* (2013.01); *G01N 33/0037* (2013.01)

(58) Field of Classification Search
  CPC .............. G01N 33/00; G01N 33/0004; G01N 33/0009; G01N 33/0037; G01N 33/007;
  (Continued)

(56) References Cited

U.S. PATENT DOCUMENTS 4,653,998 A * 3/1987 Sohma .................... F23N 5/082
                                                   431/12
4,969,408 A * 11/1990 Archer .................... F23N 5/006
                                                   700/285
(Continued)

FOREIGN PATENT DOCUMENTS

EP    2423590 A2    2/2012
JP    61-191950 A   8/1986
(Continued)

OTHER PUBLICATIONS

US EPA (Environmental Protection Agency) Eastern Research Group. "I. Air Emissions Inventory Improvement Program (EIIP)., vol. II Chapter 2" (Jan. 2001). (Year: 2001).*

*Primary Examiner* — David L Singer
*Assistant Examiner* — Fatemeh Esfandiari Nia
(74) *Attorney, Agent, or Firm* — WHDA, LLP (57) ABSTRACT

An analysis condition adjusting device of a fuel analyzer includes a first NOx computing unit for calculating a reference NOx estimation value using a previously obtained first industrial analysis value of a fuel sample, a second NOx computing unit for calculating a plurality of varied NOx estimation value by varying a value of each of components of the first industrial analysis value, a NOx error computing unit for computing an error as a NOx error between the reference NOx estimation value and each of the varied NOx estimation values, an analysis error tolerance range setting unit for setting an analysis error tolerance range of each of the components based on a value variation amount of each of the components, the value variation amount being defined such that the NOx error is within a tolerance range, and an analysis condition adjusting unit for adjusting an analysis condition of a fuel analyzer.

7 Claims, 7 Drawing Sheets

(58) Field of Classification Search
CPC ........... G01N 33/0006; G01N 33/0073; G01N 33/225; F22B 35/00
See application file for complete search history.

(56) References Cited

U.S. PATENT DOCUMENTS

| | | | | |
|---|---|---|---|---|
| 6,522,994 | B1 * | 2/2003 | Lang | F22B 35/18 |
| | | | | 700/274 |
| 9,127,836 | B2 * | 9/2015 | Matsumoto | F23D 1/005 |
| 2010/0031858 | A1 * | 2/2010 | Orii | F23C 7/02 |
| | | | | 110/297 |
| 2011/0197831 | A1 * | 8/2011 | Ohyatsu | G01F 1/7046 |
| | | | | 122/6 R |
| 2012/0152158 | A1 * | 6/2012 | Matsumoto | F23C 6/045 |
| | | | | 110/297 |
| 2016/0320058 | A1 * | 11/2016 | Kortela | G05B 15/02 |

FOREIGN PATENT DOCUMENTS

| | | | |
|---|---|---|---|
| JP | 2656418 | B2 * | 9/1997 |
| JP | 2011106790 | A * | 6/2011 |
| JP | 5352548 | B2 | 11/2013 |
| JP | 5357714 | B2 | 12/2013 |

* cited by examiner

ANALYSIS CONDITION ADJUSTING DEVICE OF SIMPLE FUEL ANALYZER

TECHNICAL FIELD

The present invention relates to a simple analyzer for analyzing fuel (hereinafter referred to as a simple fuel analyzer) and an analysis condition adjusting device thereof.

BACKGROUND ART

Thermal power plants having a boiler and a steam turbine as main components are required to keep NOx in exhaust gas and unburned combustible content in ash (hereinafter sometimes referred to simply as "unburned combustible") in exhaust gas to be under or equal to specified values (for example, PTL 1).

In general, NOx and unburned combustible contents in exhaust gas are estimated using an industrial analysis value of fuel, and the operating variable of the operating end of a boiler is adjusted to keep their estimation values to be under or equal to specified values, thereby adjusting the combustion state in a furnace, so that the NOx and unburned combustible contents in exhaust gas are kept to be under or equal to the specified values.

CITATION LIST

Patent Literature

[PTL 1]
the Publication of Japanese Patent No. 5357714

SUMMARY OF INVENTION

Technical Problem

For estimation of NOx and unburned combustible contents in the above described combustion adjustment, an industrial analysis value of fuel is used as a parameter.

Conventionally, to obtain high-accuracy industrial analysis value of fuel, a method that takes several days to one week or so has been used. For this reason, the actual characteristic of fuel supplied during plant operation may be different from the characteristic of fuel used in analysis, so the analysis result deviates from the actual fuel, which can cause analysis error. Because fuel analysis error affects estimation of NOx and unburned combustible contents, there has been a possibility that desired estimation accuracy cannot be obtained in estimation of NOx and unburned combustible contents.

The present invention has been made in view of the above described circumstances, and an object of the present invention is to provide an analysis condition adjusting device of a simple fuel analyzer, whereby fuel to be input to a boiler can be analyzed with a certain degree of analysis accuracy or more, and the time taken to obtain an industrial analysis value of fuel can be shortened.

Solution to Problem

A first aspect of the present invention is an analysis condition adjusting device of a simple fuel analyzer including: a first NOx computing unit for calculating a NOx estimation value as a reference NOx estimation value by inputting a previously obtained first industrial analysis value of a fuel sample into a NOx estimating equation for estimating an amount of NOx in exhaust gas; a second NOx computing unit for calculating a plurality of varied NOx estimation values by varying a value of each of components of the first industrial analysis value and inputting the varied value of each component into the NOx estimating equation; a NOx error computing unit for computing an error of each of the varied NOx estimation values relative to the reference NOx estimation value, as a NOx error; an analysis error tolerance range setting unit for determining a value variation amount of each of the components such that the NOx error is within a tolerance range, and setting an analysis error tolerance range of each of the components based on the determined value variation amount; an analysis error computing unit for computing, for each component, an analysis error between a value of each of components of a second industrial analysis value of the fuel sample analyzed by the simple fuel analyzer and the value of each component of the first industrial analysis value; a determining unit for determining whether or not the analysis error for each component is within the analysis error tolerance range set for each component; and an analysis condition adjusting unit for adjusting an analysis condition of the simple fuel analyzer until the analysis error for each component becomes the analysis error tolerance range set for each component.

According to the analysis condition adjusting device in the above described configuration, a difference between a reference NOx estimation value calculated using a previously obtained first industrial analysis value of a fuel sample in a NOx estimation equation and a plurality of varied NOx estimation values estimated using a varied value of each component of the industrial analysis value is computed as a NOx error, and a value variation amount is determined for each component such that the NOx error is within a tolerance range. Thereby, a value variation amount in a case when a NOx estimation value within a tolerance range is obtained, in other words, an analysis error range allowed for obtaining a NOx estimation value within the tolerance range is determined for each component. Then, a difference between the value of each of the components of the fuel sample from the first industrial analysis value and the value of each of the components of the fuel sample from the simple fuel analyzer is computed as an analysis error, and an analysis condition of the simple fuel analyzer is adjusted until the analysis error becomes within an analysis error tolerance range.

As described above, the analysis error tolerance range is determined for keeping the estimation error of the NOx estimation value within a tolerance range, and the analysis error between the first industrial analysis value and the second industrial analysis value of the fuel sample analyzed by the simple fuel analyzer is kept within the analysis error tolerance range, so that the estimation error of NOx estimation value estimated using the analysis result of the simple fuel analyzer can be kept within the tolerance range.

The above described "first industrial analysis value" refers to a result of analysis of a fuel sample using an industrial analysis method that satisfies required analysis accuracy. Examples of such industrial analysis methods include industrial analysis methods compliant with "JIS M 8812-2004", "ISO 562", "ISO 687", and "ISO 5071-1".

The above described analysis condition adjusting device may include: a first unburned combustible computing unit for calculating an unburned combustible estimation value as a reference unburned combustible estimation value by inputting the previously obtained first industrial analysis value of the fuel sample into an unburned combustible estimating equation for estimating an amount of unburned combustible in exhaust gas; a second unburned combustible computing unit for calculating a plurality of varied unburned combustible estimation values by varying a value of each of components of the first industrial analysis value and inputting the varied value of each component into the unburned combustible estimating equation; and an unburned combustible error computing unit for computing an error of each of the varied unburned combustible estimation values relative to the reference unburned combustible estimation value, as an unburned combustible error, wherein the analysis error tolerance range setting unit determines a value variation amount of each of the components such that the NOx error and the unburned combustible error are within their tolerance ranges, and setting an analysis error tolerance range of each of the components based on the determined value variation amount.

According to the analysis condition adjusting device in the above described configuration, since an error tolerance range for each component is determined in consideration also of estimation accuracy for unburned combustible, estimated errors of a NOx estimation value and an unburned combustible estimation value which are estimated using an analysis result obtained by the simple fuel analyzer can be kept within their tolerance ranges, and stable estimation accuracy can be ensured.

A second aspect of the present invention is an analysis condition adjusting device of a simple fuel analyzer including: a first unburned combustible computing unit for calculating an unburned combustible estimation value as a reference unburned combustible estimation value by inputting a previously obtained first industrial analysis value of a fuel sample into an unburned combustible estimating equation for estimating an amount of unburned combustible in exhaust gas; a second unburned combustible computing unit for calculating a plurality of varied unburned combustible estimation values by varying a value of each of components of the first industrial analysis value and inputting the varied value of each component into the unburned combustible estimating equation; an unburned combustible error computing unit for computing an error of each of the varied unburned combustible estimation values relative to the reference unburned combustible estimation value, as an unburned combustible error; an analysis error tolerance range setting unit for determining a value variation amount of each of the components such that the unburned combustible error is within a tolerance range, and setting an analysis error tolerance range of each of the components based on the determined value variation amount; an analysis error computing unit for computing, for each component, an analysis error between a value of each of components of a second industrial analysis value of the fuel sample analyzed by the simple fuel analyzer and the value of each component of the first industrial analysis value; a determining unit for determining whether or not the analysis error for each component is within the analysis error tolerance range set for each component; and an analysis condition adjusting unit for adjusting an analysis condition of the simple fuel analyzer until the analysis error for each component becomes within the analysis error tolerance range set for each component.

According to the analysis condition adjusting device in the above described configuration, a difference between a reference unburned combustible estimation value calculated using a previously obtained first industrial analysis value of a fuel sample in an unburned combustible estimation equation and a plurality of varied unburned combustible estimation values estimated using a varied value of each of components of the industrial analysis value is computed as an unburned combustible error, and a value variation amount is determined for each component such that the unburned combustible error is within a tolerance range. Thereby, a value variation amount in a case when an unburned combustible estimation value within a tolerance range is obtained, in other words, an analysis error range allowed for obtaining an unburned combustible estimation value within the tolerance range is determined for each component. Then, a difference between the value of each component of the previously obtained first industrial analysis value of the fuel sample and the value of each component of the fuel sample from the simple fuel analyzer is computed as an analysis error, and an analysis condition of the simple fuel analyzer is adjusted until the analysis error becomes within an analysis error tolerance range.

As described above, the analysis error tolerance range is determined for keeping the estimation error of the unburned combustible estimation value within a tolerance range, and the analysis error between the first industrial analysis value and the second industrial analysis value of the fuel sample analyzed by the simple fuel analyzer is kept within the analysis error tolerance range, so that the estimation error of unburned combustible estimation value estimated using the analysis result of the simple fuel analyzer can be kept within the tolerance range.

A third aspect of the present invention is a simple fuel analyzer wherein an analysis condition of the simple fuel analyzer is adjusted using any one of the above described analysis condition adjusting devices.

A fourth aspect of the present invention is a controller for controlling a boiler, the controller including: the above described simple fuel analyzer for analyzing a fuel supplied to the boiler; a NOx estimating unit for estimating an amount of NOx in exhaust gas to be exhausted from the boiler, by using in a NOx estimating equation an analysis result obtained by the simple fuel analyzer; an unburned combustible estimating unit for estimating an amount of unburned combustible in the exhaust gas to be exhausted from the boiler, by using in an unburned combustible estimating equation the analysis result obtained by the simple fuel analyzer; and a combustion adjusting unit for controlling an operation end for adjusting a combustion state of the boiler, such that the amount of NOx estimated by the NOx estimating unit and the amount of unburned combustible estimated by the unburned combustible estimating unit are within their tolerance ranges.

A fifth aspect of the present invention is a method for adjusting an analysis condition of a simple fuel analyzer, the method including: a first NOx computing step of calculating a NOx estimation value as a reference NOx estimation value by inputting a previously obtained first industrial analysis value of a fuel sample into a NOx estimating equation for estimating an amount of NOx in exhaust gas; a second NOx computing step of calculating a plurality of varied NOx estimation values by varying a value of each of components of the first industrial analysis value and inputting the varied value of each component into the NOx estimating equation; a NOx error computing step of computing an error of each of the varied NOx estimation values relative to the reference NOx estimation value, as a NOx error; an analysis error tolerance range setting step of determining a value variation amount of each of the components such that the NOx error is within a tolerance range, and setting an analysis error tolerance range of each of the components based on the determined value variation amount; an analysis error computing step of computing, for each component, an analysis error between a value of each of components of a second industrial analysis value of the fuel sample analyzed by the simple fuel analyzer and the value of each component of the first industrial analysis value; a determining step of determining whether or not the analysis error for each component is within the analysis error tolerance range set for each component; and an analysis condition adjusting step of adjusting the analysis condition of the simple fuel analyzer until the analysis error for each component becomes within the analysis error tolerance range set for each component.

A sixth aspect of the present invention is a method for adjusting an analysis condition of a simple fuel analyzer, the method including: a first unburned combustible computing step of calculating an unburned combustible estimation value as a reference unburned combustible estimation value by inputting a previously obtained first industrial analysis value of a fuel sample into an unburned combustible estimating equation for estimating an amount of unburned combustible in exhaust gas; a second unburned combustible computing step of calculating a plurality of varied unburned combustible estimation values by varying a value of each of components of the first industrial analysis value and inputting the varied value of each component into the unburned combustible estimating equation; an unburned combustible error computing step of computing an error of each of the varied unburned combustible estimation values relative to the reference unburned combustible estimation value, as an unburned combustible error; an analysis error tolerance range setting step of determining a value variation amount of each of the components such that the unburned combustible error is within a tolerance range, and setting an analysis error tolerance range of each of the components based on the determined value variation amount; an analysis error computing step of computing, for each component, an analysis error between a value of each of components of a second industrial analysis value of the fuel sample analyzed by the simple fuel analyzer and the value of each component of the first industrial analysis value; a determining step of determining whether or not the analysis error for each component is within the analysis error tolerance range set for each component; and an analysis condition adjusting step of adjusting the analysis condition of the simple fuel analyzer until the analysis error for each component becomes within the analysis error tolerance range set for each component.

Advantageous Effects of Invention

According to the present invention, there are effects that fuel to be input to a boiler can be analyzed with a certain degree of analysis accuracy or more, and the time taken to obtain an industrial analysis value of fuel can be shortened.

DESCRIPTION OF THE EMBODIMENTS

Embodiments of a simple analyzer and an analysis condition adjusting device thereof according to the present invention will be described below with reference to the drawings. In the following description, a solid fuel fired boiler, particularly, a swirling combustion boiler provided with a pulverized coal burner fueled with pulverized coal (coal as powdered solid fuel) will be described as an example boiler to which a simple analyzer and an analysis condition adjusting device thereof according to one embodiment of the present invention is applied. However, the simple analyzer and the analysis condition adjusting device thereof according to one embodiment of the present invention is not limited to be applied to this example, and can be widely applied to boilers that use coal or the like as fuel.

Figure 1:
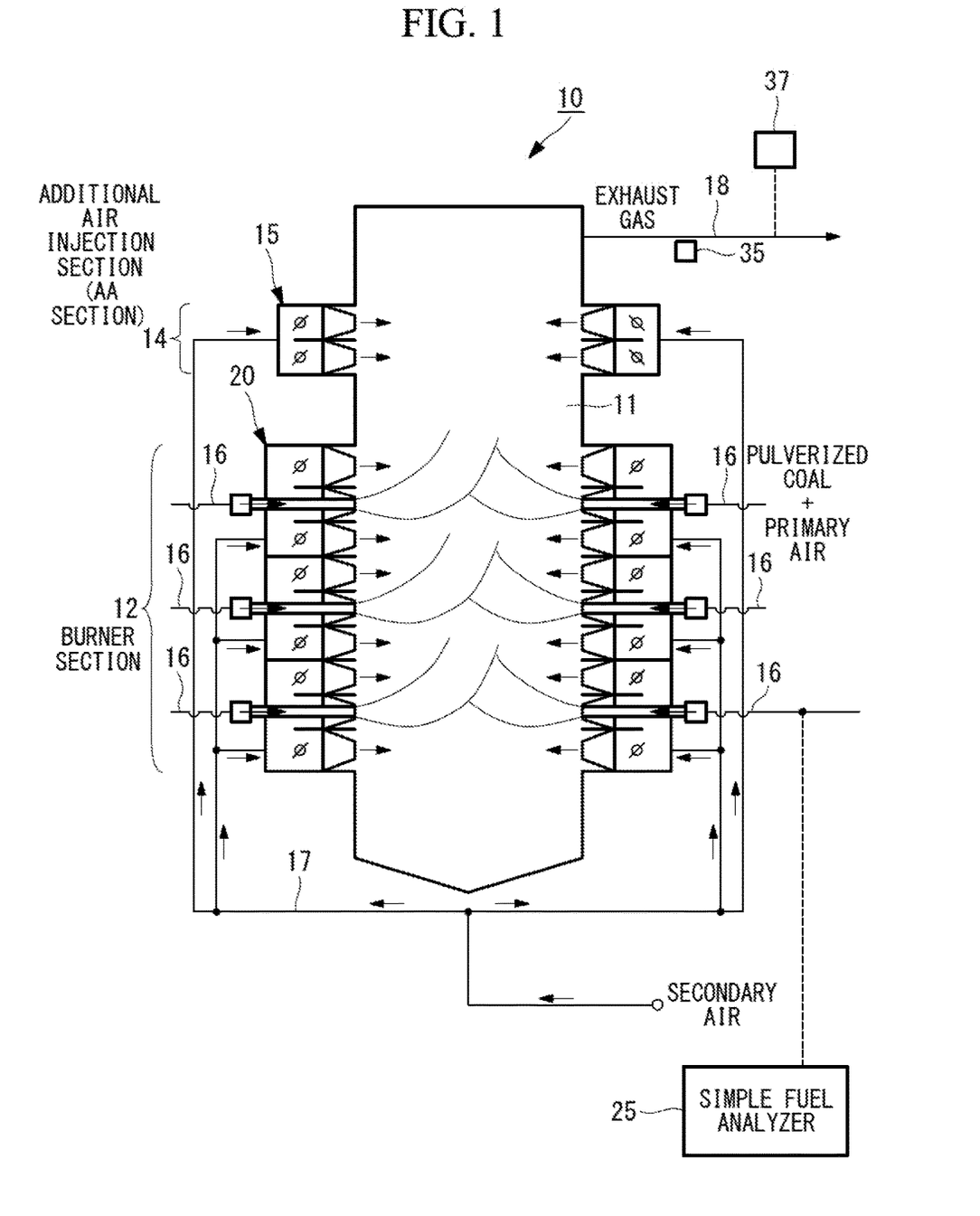
FIG. 1 is a longitudinal sectional view of a boiler according to one embodiment of the present invention.
Figure 2:
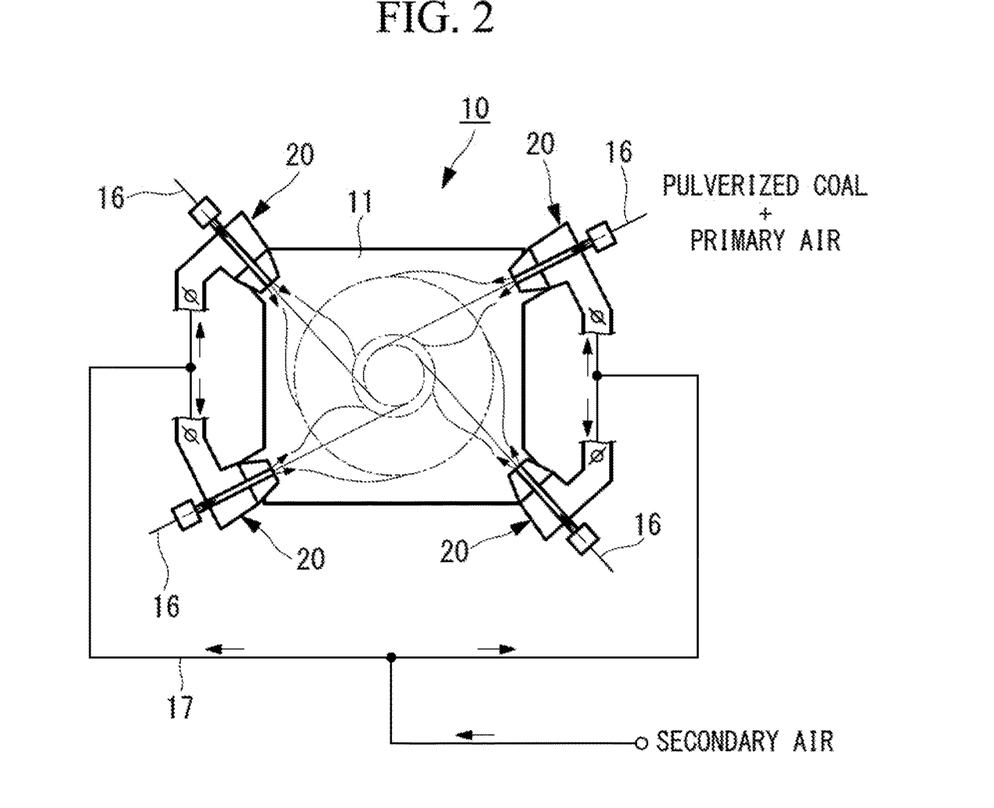
FIG. 2 is a cross (horizontal) sectional view of FIG. 1.

FIG. 1 is a longitudinal sectional view of a boiler 10 according to one embodiment of the present invention, and FIG. 2 is a cross (horizontal) sectional view of FIG. 1. As shown in FIG. 1, the boiler 10 injects air into a furnace 11 in multiple stages, so that an area from a burner section 12 to an additional air injection section (hereinafter referred to as "AA section") 14 is made under a reducing atmosphere, so as to reduce NOx in combustion exhaust gas.

As shown in FIG. 1 and FIG. 2, the boiler 10 includes a pulverized coal burner 20 that injects pulverized coal (pulverized fuel), and an additional air injection nozzle 15 that injects additional air into the AA section 14. Pulverized coal is solid fuel such as coal crushed by a mill (not shown). The pulverized coal burner 20 is connected with pulverized coal mixture gas transport pipes 16 that transport pulverized coal mixed with primary air from the mill, and with an air supply duct 17 for supplying a part of secondary air to around the pulverized coal mixture gas transport pipes 16. The additional air injection nozzle 15 of the AA section 14 is connected with an air supply duct 17 for supplying a part of the secondary air. The air supply duct 17 is supplied with the secondary air supplied from an air blower (not shown) and preheated to a predetermined temperature by an air preheater (not shown). In this way, the boiler 10 according to the present embodiment includes the burner section 12 in which the pulverized coal burner 20 is disposed at each corner portion in the horizontal direction (see FIG. 2) of the boiler 10 at each of stages provided vertically one above the other, and employs a swirling combustion boiler scheme (see FIG. 2) in which pulverized coal fuel and air are injected from the pulverized coal burner 20 into the furnace 11 to form swirling flame.

Figure 3:
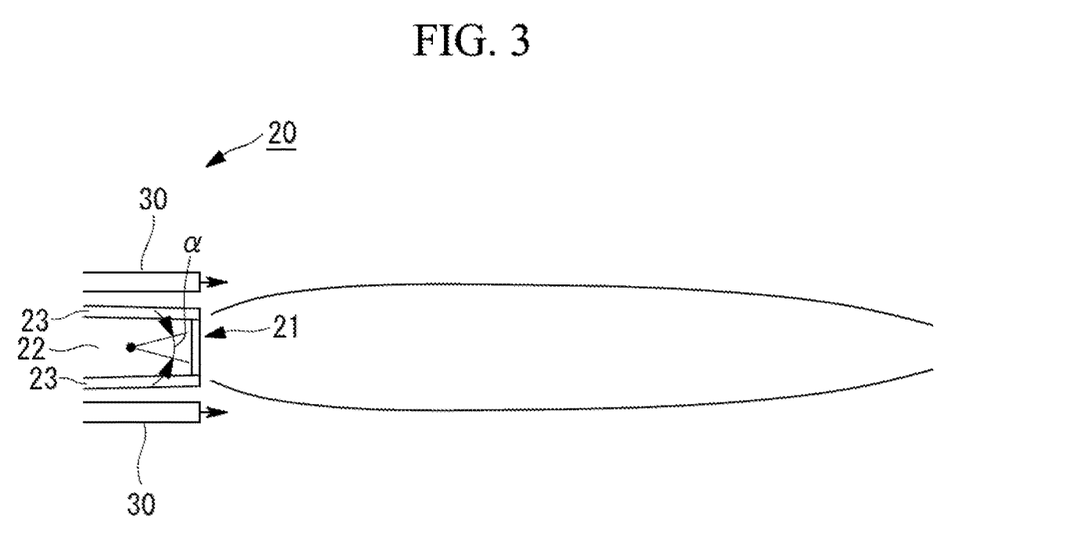
FIG. 3 is an enlarged view of the pulverized coal burner shown in FIG. 1.
Figure 4:
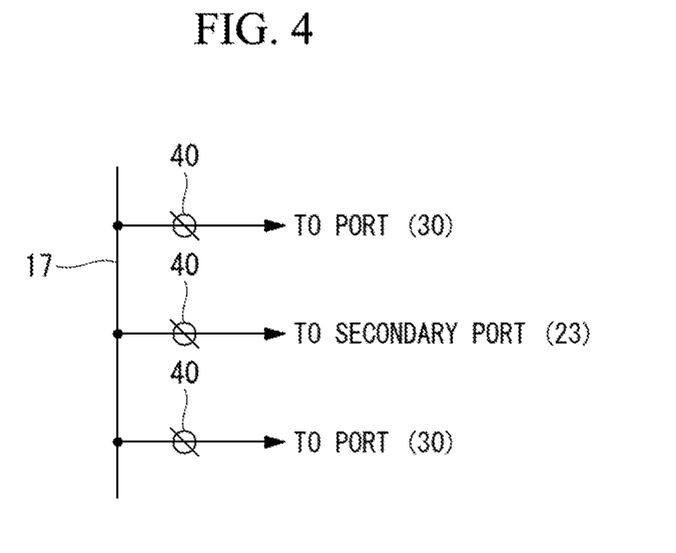
FIG. 4 is a schematic view of an air supply system supplying air to a fuel burner included in a pulverized coal burner according to one embodiment of the present invention.

FIG. 3 is an enlarged view of the pulverized coal burner 20 shown in FIG. 1. As shown in FIG. 3, the pulverized coal burner 20 includes a fuel burner 21 that injects pulverized coal and primary air, and ports 30 which are used for injecting secondary air and disposed above and below the fuel burner 21. In order to allow airflow adjustment in each port, the ports 30 are each provided with a damper 40 able to adjust its opening degree as an airflow adjustment means for each secondary air supply line branched from the air supply duct 17, for example, as shown in FIG. 4.

As shown in FIG. 3, the burner 21 includes a rectangular primary port 22 that injects pulverized coal transported by primary air, and a secondary port 23 that is provided so as to surround the primary port 22 and that injects part of secondary air. The secondary port 23 is also provided with the damper 40 able to adjust its opening degree as an airflow adjustment means, as shown in FIG. 4.

The fuel burner 21 is configured to be angle adjustable. Specifically, as shown in FIG. 3, in order to adjust the temperature of steam generated by the boiler 10 to a predetermined value, the fuel burner 21 can change the angle α of gas blowing out from the tip of the fuel burner 21 with respect to horizontal direction (burner angle α) vertically up and down, so that the position of a swirling flame formed in the furnace 11 and at each stage of the burner section 12 can be changed.

As shown in FIG. 1, the boiler 10 is provided with an exhaust gas flow path 18 for transporting combustion exhaust gas to downstream equipment. The exhaust gas flow path 18 is provided with unburned combustible measuring instrument 35 for measuring unburned combustible fuel contained in exhaust gas exhausted from the boiler 10. One example of this unburned combustible measuring instrument 35 is an unburned combustible measuring instrument using the LIBS method (Laser Induced Breakdown Spectroscopy), which samples ash flowing in the exhaust gas flow path 18, forms plasma of the sampled ash by laser irradiation, and performs spectroscopic analysis on the plasma light to measure the component concentration of ash. This unburned combustible measuring instrument 35 can measure unburned combustible in ash in substantially real time.

Further, the exhaust gas flow path 18 is provided with a NOx measuring instrument 37 that measures NOx the amount of NOx (NOx concentration) in the exhaust gas. Examples of the NOx measuring instrument 37 include measuring instruments using an infrared absorption method, a chemiluminescence method, an ultraviolet absorption method and the like.

An unburned combustible measurement value measured by the unburned combustible measuring instrument 35 and a NOx measurement value measured by the NOx measuring instrument 37 are output to a controller 50 (see FIG. 5) for controlling the boiler 10.

The pulverized coal mixture gas transport pipes 16 for injecting fuel in the boiler 10 is provided with a simple fuel analyzer 25 that samples pulverized coal to be supplied to the boiler 10 and performs industrial analysis of the pulverized coal on site.

The simple fuel analyzer 25 can obtain analysis result in 30 minutes to two hours. Examples of the simple fuel analyzer 25 include an analyzer that performs heat treatment using a hearing furnace having a thermosbalance on different conditions by switching the atmosphere in the furnace between a oxidation state and a non-oxidation state, thereby obtaining a different kinds of content (moisture content, volatile content, fixed carbon content, ash content) in a series of processes, and an analyzer that employs an analysis method excluding moisture measurement which is time-consuming for drying. One example of an analyzer for performing fuel analysis using a hearing furnace having a thermosbalance is a device disclosed in Japanese Unexamined Patent Application, Publication No. Sho 61-191950. The simple fuel analyzer 25 used on site is an analyzer ensured to have a certain degree of analysis accuracy because its analysis condition is adjusted in advance by an analysis condition adjusting device 60 as described later. Details of an analysis condition adjusting device 60 will be described later.

The controller 50 is a controller for controlling the entire boiler, and is composed of, for example, a CPU (Central Processing Unit), a main memory such as a RAM (Random Access Memory), an auxiliary memory such as a ROM (Read Only Memory), a computer readable storage medium such as an HDD, and the like. A series of processes for realizing various functions described later which the controller has is, for example, stored in a program format in a storage medium or the like, and the CPU loads the program into the main memory and executes information processing and arithmetic processing to realize the various functions. As an applicable form, the program may be pre-installed in a ROM or other storage media, may be stored in a computer readable storage medium and provided as the storage medium, may be distributed via a wired or wireless communication means, or the like. The computer readable storage medium may be a magnetic disk, a magneto-optical disk, a CD-ROM, a DVD-ROM, a semiconductor memory, or the like.

The controller 50 has a plurality of functions, for example, a load control function of controlling the number of mills (not shown) and the number of operating fuel burners 21 based on a ratio of their steam generation amount to a rated steam generation amount of the boiler 10 (hereinafter referred to as "load"), and a combustion adjusting function of adjusting a combustion state in the furnace 11 in order to reduce NOx and unburned combustible contents in exhaust gas exhausted from the boiler 10 to specified values or less.

Figure 5:
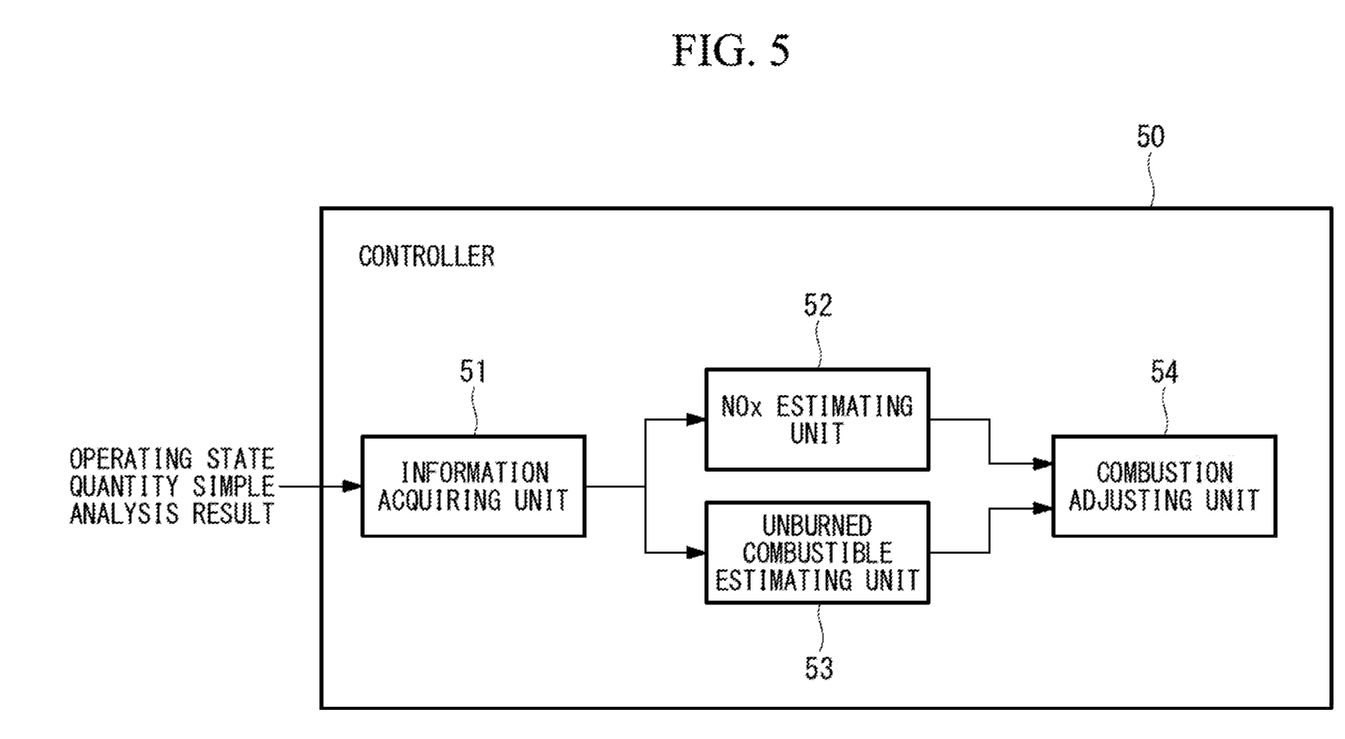
FIG. 5 is a functional block diagram of a controller for a boiler according to one embodiment of the present invention.

FIG. 5 is a functional block diagram showing a function mainly about combustion adjustment, which is extracted for illustrative purpose from the functions of the controller 50. As shown in FIG. 5, the controller 50 includes an information acquiring unit 51, a NOx estimating unit 52, an unburned combustible estimating unit 53, and a combustion adjusting unit 54.

The information acquiring unit 51 acquires input information required for estimating NOx and unburned combustible contents. The input information acquired by the information acquiring unit 51 includes mainly operating state quantity and fuel information.

The operating state quantity is parameters about the operating state of the boiler 10, and includes, for example, a distribution ratio of secondary air between the burner 12 and the AA section 14, a gas temperature, a gas property, and the like.

The fuel information includes the moisture content, volatile content, fixed carbon content, ash content, and the like of pulverized coal, and is analysis values measured by the simple fuel analyzer 25 on site. The fuel information also includes a particle diameter, fineness, and the like.

The NOx estimating unit 52 estimates the amount of NOx in exhaust gas exhausted from the boiler 10 by substituting into a NOx estimating equation held in advance, the operating state quantity and fuel information acquired by the information acquiring unit 51 and boiler design information held in advance. This design information is information on design of the boiler 10, and includes, for example, the shape and the number of pulverized coal burners 20 provided in the boiler 10, the shape of the boiler 10, and the like.

The NOx estimating equation used by the NOx estimating unit 52 is, for example, an arithmetic equation constructed based on past operating data, and includes the above described boiler design information, operating state quantity, and fuel information as parameters.

The unburned combustible estimating unit 53 estimates the amount of unburned combustible in exhaust gas exhausted from the boiler 10 by substituting into an unburned combustible estimating equation held in advance, the operating state quantity and fuel information acquired by the information acquiring unit 51 and boiler design information held in advance. This design information is the same as the above described information used by the NOx estimating unit 52, and may therefore use the information held by the NOx estimating unit 52.

The unburned combustible estimating equation used by the unburned combustible estimating unit 53 is, for example, an arithmetic equation constructed based on past operating data, and includes the above described boiler design information, operating state quantity, and fuel information as parameters.

The combustion adjusting unit 54 determines an operating variable of each operating end of the boiler 10 based on the amount of NOx estimated by the NOx estimating unit 52 (hereinafter referred to as "NOx estimation value") and the amount of unburned combustible estimated by the unburned combustible estimating unit 53 (hereinafter referred to as "unburned combustible estimation value"), so that the NOx estimation value and the unburned combustible estimation value are less than or equal to specified values. For example, the combustion adjusting unit 54 adjusts the ratio of secondary air between the burner section 12 and the AA section 14 by controlling the opening degree of the damper 40, and changes the position of a swirling flame in the furnace 11 by controlling the burner angle α of the fuel burner 21. Thereby, the combustion state in the furnace 11 is changed so that the amount of NOx and the amount of unburned combustible in the exhaust gas can be controlled.

Figure 6:
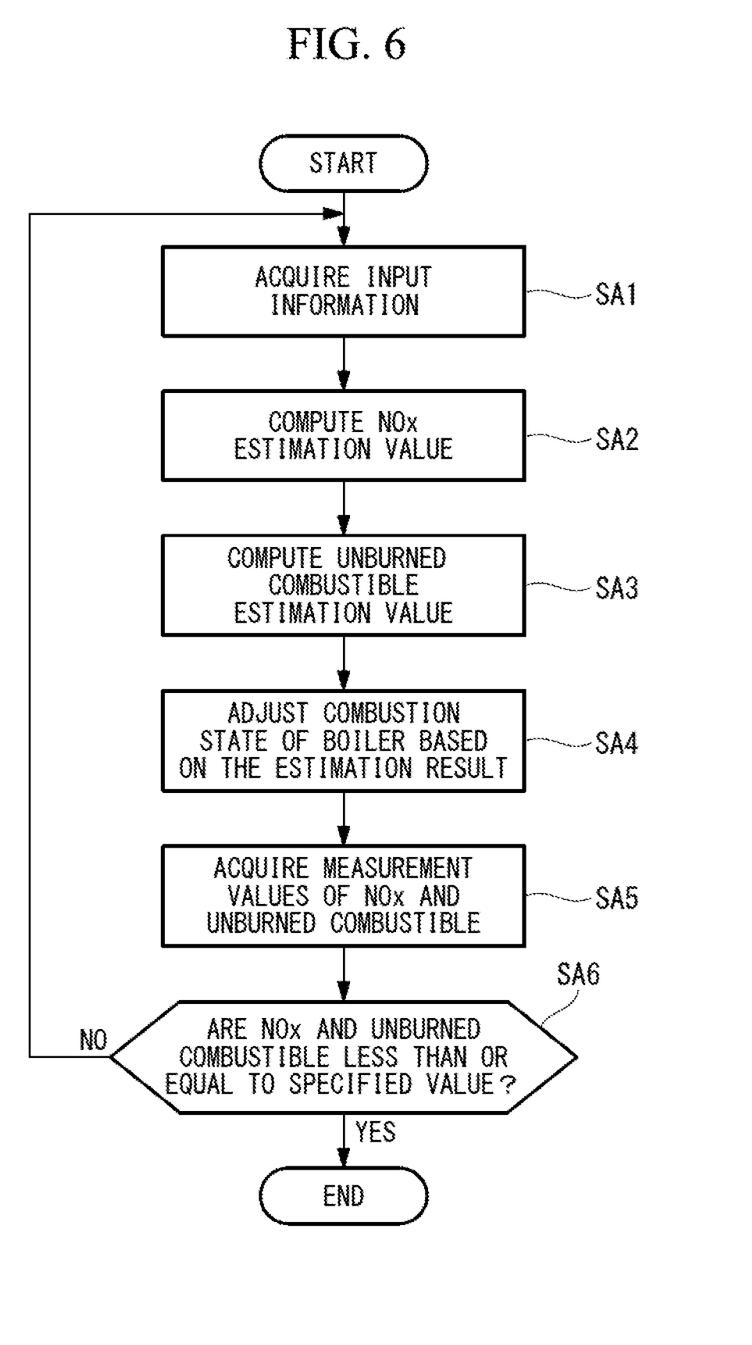
FIG. 6 is a flowchart illustrating a procedure of a combustion adjusting process performed by the controller for the boiler according to one embodiment of the present invention.

Next, a combustion adjusting method implemented by the controller 50 will be described briefly with reference to FIG. 6. FIG. 6 is a flowchart illustrating one example of a processing procedure of a combustion adjusting process performed by the controller 50.

First, the information acquiring unit 51 acquires input information necessary for estimating NOx and unburned combustible contents (SA1). Thereby, an operating state quantity of the boiler 10 and a fuel analysis result obtained by the simple fuel analyzer 25 are acquired.

Subsequently, the NOx estimating unit 52 substitutes the information acquired by the information acquiring unit 51 into the NOx estimating equation to compute a NOx estimation value (SA2). Similarly, the unburned combustible estimating unit 53 substitutes the information acquired by the information acquiring unit 51 into the unburned combustible estimating equation to compute an unburned combustible estimation value (SA3).

Then, the combustion adjusting unit 54 adjusts the combustion state of the boiler 10 by controlling the dampers 40 and the burner angles α of the fuel burners 21 based on the NOx estimation value and the unburned combustible estimation value (SA4). As the combustion state of the boiler is changed, the amount of NOx and the amount of unburned combustible in the exhaust gas to be exhausted from the boiler 10 change.

The combustion adjusting unit 54 acquires an unburned combustible measurement value from the unburned combustible measuring instrument 35 as well as a NOx measurement value from the NOx measuring instrument 37 (SA5), and determines whether or not these measurement values are both less than or equal to specified values (SA6).

If these values are greater than the specified values as a result, the control returns to step SA1, and repeats the above described process. If both of the unburned combustible measurement value and the NOx measurement value are determined to be less than or equal to the environmental specified values in step SA6, this combustion adjusting process is terminated.

The controller 50 suppresses the amount of NOx and unburned combustible contents to be less than or equal to the specified values, for example, by repeating the combustion adjusting process shown in FIG. 6 at a predetermined time interval.

Next, the simple fuel analyzer 25 used on site and the analysis condition adjusting device 60 of the simple fuel analyzer 25 will be described with reference to the drawings.

The simple fuel analyzer 25 can obtain analysis result in 30 minutes to two hours as described above, and one example thereof is an analyzer that employs the industrial analysis method for analyzing coal or the like disclosed in Japanese Unexamined Patent Application, Publication No. Sho 61-191950. The analysis condition adjusting device 60 is a device for ensuring the accuracy of the simple fuel analyzer 25, and adjusts an analysis condition so that, for example, the accuracy of the simple fuel analyzer 25 becomes greater than or equal to a certain degree before the simple fuel analyzer 25 is introduced for onsite analysis of the boiler 10.

The analysis condition adjusting device 60 is, for example, a computer, and includes a CPU, a main memory, an auxiliary memory, and the like as in the above described controller 50. A series of processes for realizing each unit's function described below is, for example, stored in a program format in an auxiliary storage medium, and the CPU loads the program into the main memory and executes information processing and arithmetic processing to realize the various functions. As an applicable form, the program may be pre-installed in a ROM or other storage media, may be stored in a computer readable storage medium and provided as the storage medium, may be distributed via a wired or wireless communication means, or the like. The computer readable storage medium may be a magnetic disk, a magneto-optical disk, a CD-ROM, a DVD-ROM, a semiconductor memory, or the like.

Figure 7:
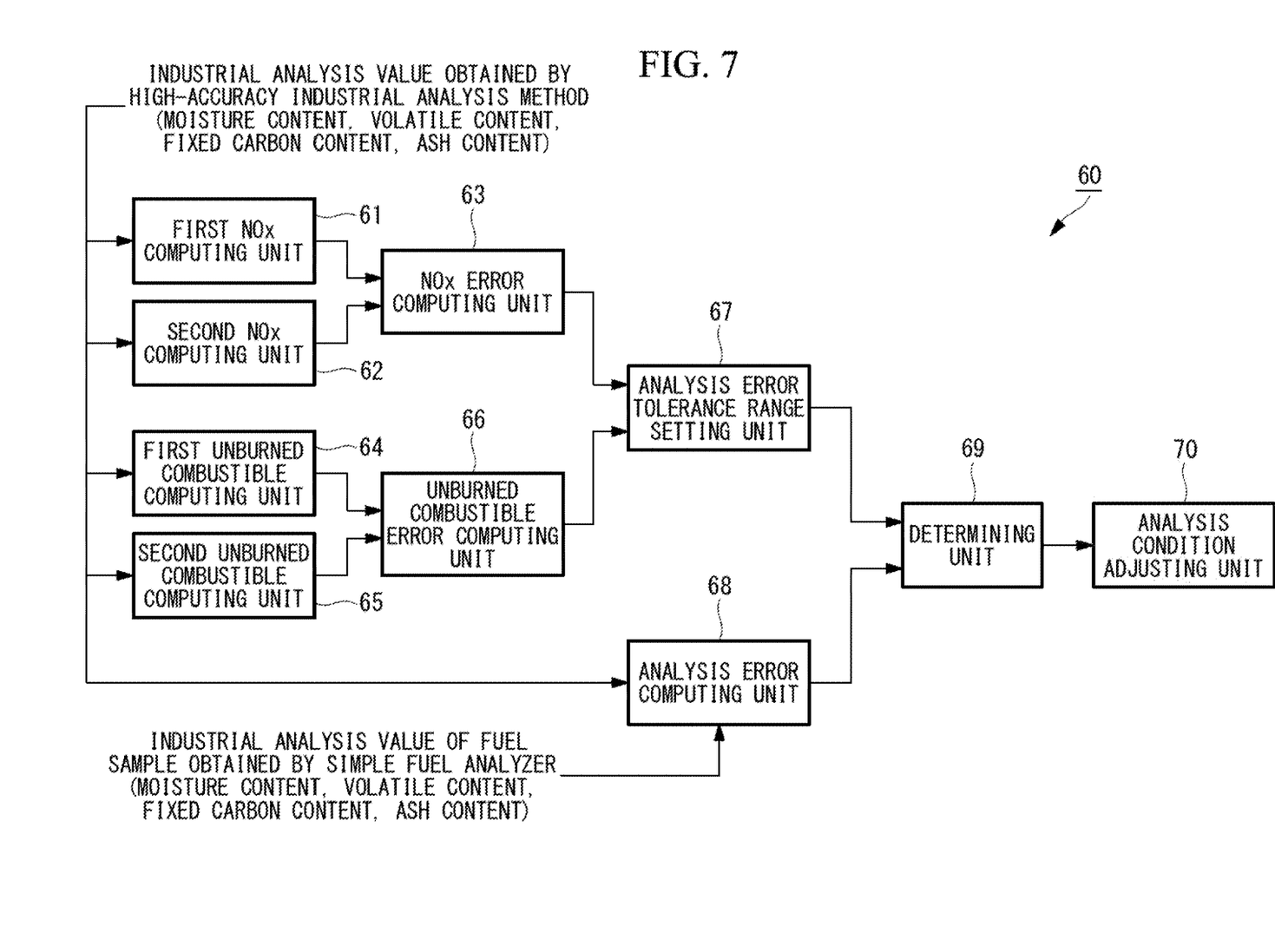
FIG. 7 is a functional block diagram of an analysis condition adjusting device of a simple analyzer according to one embodiment of the present invention.

FIG. 7 is a functional block diagram of the analysis condition adjusting device 60 according to one embodiment of the present invention. As shown in FIG. 7, the analysis condition adjusting device 60 includes as main components, a first NOx computing unit 61, a second NOx computing unit 62, a NOx error computing unit 63, a first unburned combustible computing unit 64, a second unburned combustible computing unit 65, an unburned combustible error computing unit 66, an analysis error tolerance range setting unit 67, an analysis error computing unit 68, a determining unit 69, and an analysis condition adjusting unit 70.

First, as preparation for performing adjustment of an analysis condition by the analysis condition adjusting device 60, a sample is prepared This sample is a sample of fuel to be used for the boiler 10, and in the present embodiment, pulverized coal is used as this sample. Since combustion states of pulverized coal vary depending on a component such as a moisture content contained in the coal, it is preferable to prepare a plurality of types of pulverized coal to take such solid variation into account. In the following description, a case where three samples, pulverized coal A, pulverized coal B and pulverized coal C, are prepared will be described as a specific example.

These pulverized coals A to C are analyzed using an industrial analysis method that is different from the simple fuel analyzer 25 and that has higher analysis accuracy (hereinafter referred to as "high-accuracy industrial analysis method") to obtain an industrial analysis value (first industrial analysis value) in advance. Components of an industrial analysis value are, for example, moisture content, volatile content, fixed carbon content, and ash content. Example of industrial analysis methods higher than the simple fuel analyzer 25 in analysis accuracy include industrial analysis methods compliant with "JIS M 8812-2004", "ISO 562", "ISO 687", and "ISO 5071-1". Although these analysis methods take several days to one week or so to obtain analysis result, these methods can obtain industrial analysis value with higher accuracy than that of analysis result obtained by the simple fuel analyzer 25.

The first NOx computing unit 61 inputs an industrial analysis value for each component previously obtained by a high-accuracy industrial analysis method with respect to each sample (the pulverized coal A to C) into a NOx estimating equation for estimating NOx concentration, to calculate a NOx estimation value. This NOx estimating equation is the same as the NOx estimating equation used in the above described combustion adjusting process.

The first NOx computing unit 61 calculates a NOx estimation value for each sample by substituting into the NOx estimating equation, a parameter about design information, various parameters about an operating state quantity, and an industrial analysis value of the sample. A NOx estimation value calculated by the first NOx computing unit 61 is hereinafter referred to as a "reference NOx estimation value" for convenience purposes.

Design information in this context is a parameter that is about the structure and the like of the boiler 10 and unique to the boiler 10. Arbitrary operating states (for example, a rated operating state) can be assumed as various parameters of an operating state to be substituted into the NOx estimating equation, so that the assumed parameters about the operating state (for example, a distribution ratio of secondary air between the burner 12 and the AA section 14, a gas temperature, a gas property, and the like) can be substituted. Various parameters about fuel information are values of respective components of the first industrial analysis value previously obtained by the high-accuracy industrial analysis method. In the present embodiment, those parameters are moisture content, volatile content, fixed carbon content, and ash content. The various parameters about fuel information also include a particle diameter or fineness.

The second NOx computing unit 62 calculates a plurality of NOx estimation values for each sample by varying a value of each of components of the first industrial analysis value within a predetermined range and inputting the varied value of each component into the NOx estimating equation for each sample. A NOx estimation value calculated by the second NOx computing unit 62 is hereinafter referred to as a "varied NOx estimation value" for convenience purposes.

For example, the second NOx computing unit 62 obtains a plurality of varied NOx estimation values by varying a value of each component (moisture content, volatile content, fixed carbon content, ash content) of pulverized coal A by a predetermined amount to predetermined upper and lower limits, and inputting the respective varied values into the NOx estimating equation.

More specifically, the second NOx computing unit 62 varies a value of each component (moisture content, volatile content, fixed carbon content, ash content) of pulverized coal A to +5%, +10%, +15%, . . . and finally to a predetermined upper limit, as well as to −5%, −10%, −15%, . . . and finally to a predetermined lower limit, and inputs the respective varied values into the NOx estimating equation, thereby calculating a plurality of varied NOx estimation values. In this case, a value can be varied for each component, so that a degree of influence of that component to the NOx estimation value can also be obtained. The amount of variation and the upper and lower limits of variation can be arbitrarily set. The second NOx computing unit 62 performs processing also on the pulverized coal B and C in the same manner, to calculate a plurality of varied NOx estimation values for each sample. For example, if a value of each component is varied in six steps such as +5%, +10%, +15%, −5%, −10%, −15%, 4 (the number of components)×6(the number of varied values)=24 varied NOx estimation values are calculated for each sample (pulverized coal A, B, C).

The NOx error computing unit 63 computes an error of each of the varied NOx estimation values relative to the reference NOx estimation value, as a NOx error. This error may be an absolute error or a relative error. Therefore, in the case where the value of each component is varied in six steps, 24 NOx errors can be computed for each sample.

The first unburned combustible computing unit 64 calculates an unburned combustible estimation value by inputting an industrial analysis value (a first industrial analysis value) of each component previously obtained by a high-accuracy industrial analysis method with respect to each sample (the pulverized coal A to C) into an unburned combustible estimating equation for estimating unburned combustible content. This unburned combustible estimating equation is the same as the unburned combustible estimating equation used in the above described combustion adjusting process.

The first unburned combustible computing unit 64 calculates an unburned combustible estimation value for each sample by substituting into the unburned combustible estimating equation, a parameter about design information, various parameters about an operating state quantity (which are the same as the parameters used by the above described NOx estimating unit), and an industrial analysis value of each sample (pulverized coal A to C). An unburned combustible estimation value calculated by the first unburned combustible computing unit 64 is hereinafter referred to as a "reference unburned combustible estimation value" for convenience purposes.

The second unburned combustible computing unit 65 calculates a plurality of unburned combustible estimation values for each sample (pulverized coal A to C) by varying a value of each of components of the first industrial analysis value within a predetermined range and inputting the varied value of each component into the unburned combustible estimating equation for each sample. An unburned combustible estimation value calculated by the second unburned combustible computing unit 65 is hereinafter referred to as a "varied unburned combustible estimation value" for convenience purposes.

For example, the second unburned combustible computing unit 65 obtains a plurality of varied unburned combustible estimation values by varying a value of each component (moisture content, volatile content, fixed carbon content, ash content) of pulverized coal A by a predetermined amount to predetermined upper and lower limits, and inputting the respective varied values into the unburned combustible estimating equation.

More specifically, the second unburned combustible computing unit 65 varies a value of each component (moisture content, volatile content, fixed carbon content, ash content) of pulverized coal A to +5%, +10%, +15%, . . . and finally to a predetermined upper limit, as well as to −5%, −10%, −15%, . . . and finally to a predetermined lower limit, and inputs the respective varied values into the unburned combustible estimating equation, thereby obtaining a plurality of varied unburned combustible estimation values. In this case, a value can be varied for each component, so that a degree of influence of that component to the unburned combustible estimation value can also be obtained. The amount of variation and the upper and lower limits of variation can be arbitrarily set. The second unburned combustible computing unit 65 performs processing also on the pulverized coal B and C in the same manner, to calculate a plurality of varied unburned combustible estimation values for each sample. For example, if a value of each component is varied in six steps such as +5%, +10%, +15%, −5%, −10%, −15%, 4 (the number of components)×6 (the number of varied values)=24 varied unburned combustible estimation values are calculated for each sample (pulverized coal A, B, C).

The unburned combustible error computing unit 66 computes an error of each of the varied unburned combustible estimation values relative to the reference unburned combustible estimation value, as an unburned combustible error. This error may be an absolute error or a relative error. Therefore, in the case where the value of each component is varied in six steps, 24 unburned combustible errors can be computed for each sample.

The analysis error tolerance range setting unit 67 determines a value variation amount for each component such that the NOx error is within a tolerance range and the unburned combustible error is within a tolerance range, and sets an analysis error tolerance range of each component based on the determined value variation amount.

For example, the analysis error tolerance range setting unit 67 partitions the NOx error computed for each sample in the NOx error for each component, determines the maximum value of NOx error where each component is in a tolerance range (for example, within ±10 ppm), and obtains a value variation amount obtained when the maximum value of NOx error is obtained. Similarly, the analysis error tolerance range setting unit 67, for example, partitions the unburned combustible error computed for each sample in the unburned combustible error for each component, determines the maximum value of unburned combustible error where each component is in a tolerance range, and identifies a value variation amount (a variation amount of each component) obtained when the maximum value of unburned combustible error is obtained. Then, based on a result of comparison between the value variation amount obtained from the NOx error and the value variation amount obtained from the unburned combustible error, an analysis error tolerance range for each component is set.

For example, focusing on component "moisture content", since six NOx errors are calculated for each of samples (pulverized coals A, B, C), a total of 18 NOx errors are calculated. Among them, NOx errors within a predetermined tolerance value range are extracted, and among the extracted NOx errors, a NOx error having the largest value is identified. Then, the variation amount of "moisture content" value obtained when the identified NOx error is obtained (for example, +10%) is identified.

The analysis error tolerance range setting unit 67 performs similar processing also about unburned combustible error. For example, focusing on component "moisture content", since six unburned combustible errors are calculated for each of samples (pulverized coals A, B, C), a total of 18 unburned combustible errors are calculated. Among them, unburned combustible errors within a predetermined tolerance value range are extracted, and among the extracted unburned combustible errors, an unburned combustible error having the largest value is identified. Then, the variation amount of "moisture content" value obtained when the identified unburned combustible error is obtained (for example, +5%) is identified.

In this way, for example, regarding the component "moisture content", if the value variation amount of "+10%" is obtained in view of NOx error and the value variation amount of "+5%" is obtained in view of unburned combustible error, the analysis error tolerance range setting unit 67 selects a smaller value variation amount, and set an analysis error tolerance range (for example, ±5%) based on the selected variation amount. The above described process may be performed separately when the value is varied to plus side and when the value is varied to minus side to determine an error tolerance value on plus side and an error tolerance value on minus side, so that an error tolerance range may be set based on these values.

Then, the analysis error tolerance range setting unit 67 performs the above described process on other components' values "volatile content", "fixed carbon content" and "ash content" in the same manner, to set an analysis error tolerance range for each component.

The above described technique for setting an analysis error tolerance range is just one example, and other techniques may be used. For example, while NOx and unburned combustible errors having discrete values are used for setting an analysis error tolerance range in the above described example, interpolation may be performed with respect to NOx and unburned combustible errors having discrete values, and the interpolation result may be used for setting an analysis error tolerance range.

The analysis error computing unit 68 acquires an analysis result (second industrial analysis value) of each sample (pulverized coal A to C) obtained by the simple fuel analyzer, and calculates an analysis error based on the acquired analysis result from the simple fuel analyzer and the analysis result (first industrial analysis value) of each sample (pulverized coal A to C) obtained by a high-accuracy industrial analysis method.

The determining unit 69 determines whether or not the analysis error calculated by the analysis error computing unit 68 is within the analysis error tolerance range for each component set by the analysis error tolerance range setting unit 67.

If at least one component's analysis error is determined to be beyond the analysis error tolerance range by the determining unit 69, the analysis condition is assumed to be inappropriate, and the analysis condition adjusting unit 70 adjusts the analysis condition. For example, the analysis condition adjusting unit 70 changes the analysis condition by automatically adjusting at least one of a temperature holding time, a temperature increase rate, a temperature decrease rate, an atmosphere gas supply amount, a sample amount, a sample particle size, a sample pan size, a structure, and the like. An analysis condition may be automatically adjusted as described above, or may be adjusted according to an instruction, for example, when information about the analysis condition to be adjusted is input as the instruction by an operator.

After the analysis condition of the simple analyzer is adjusted, the simple analyzer in which the adjusted analysis condition is set performs analysis of samples (pulverized coal A to C). The above described adjustment of analysis condition of the simpler analyzer is repeatedly performed until analysis errors of all the component of the industrial analysis value obtained by the simple analyzer becomes within their error tolerance ranges.

Figure 8:
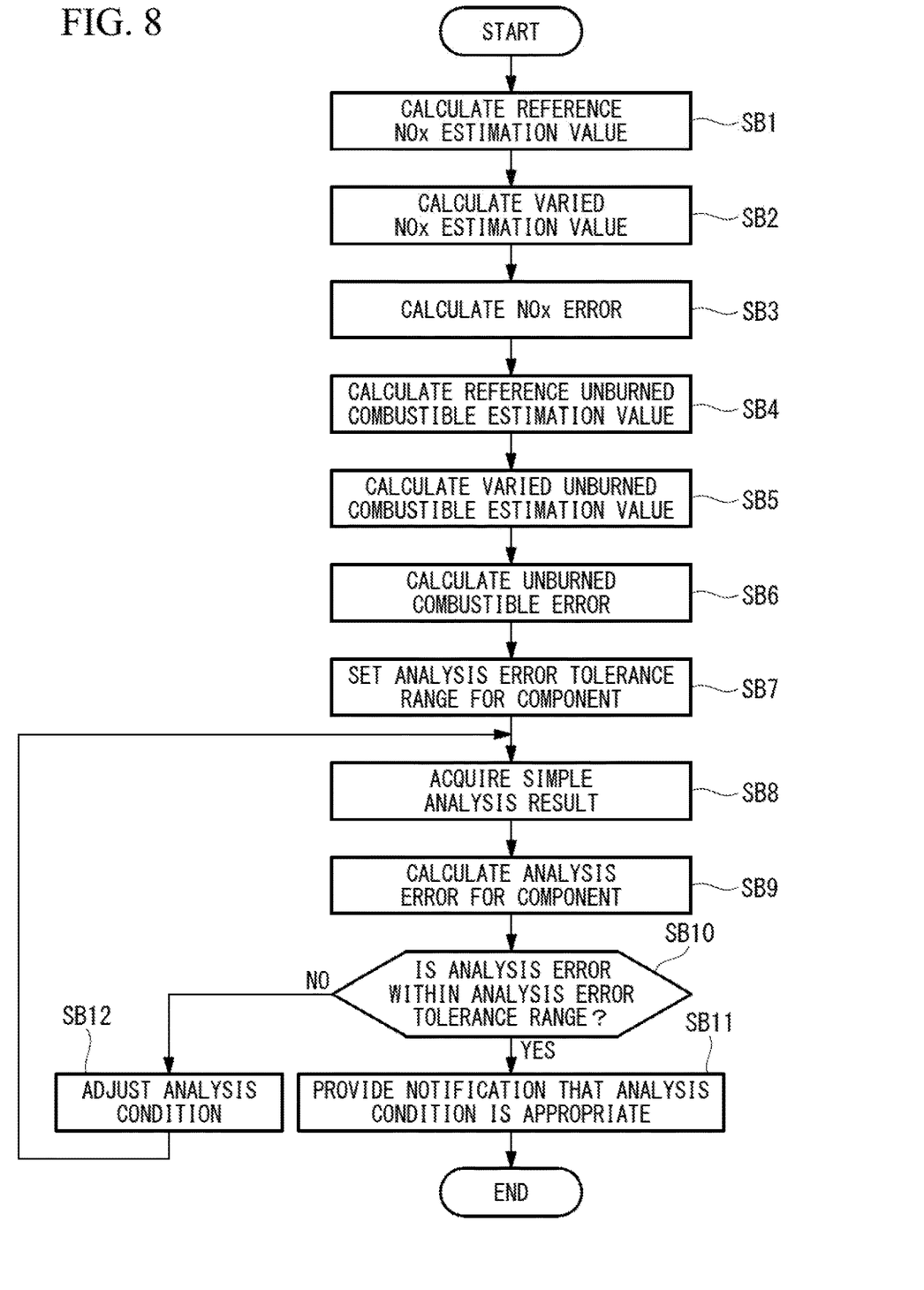
FIG. 8 is a flowchart illustrating a procedure of an analysis condition adjusting process performed by the analysis condition adjusting device of the simple analyzer according to one embodiment of the present invention.

A procedure of an analysis condition adjustment method performed by the analysis condition adjusting device 60 according to one embodiment of the present invention will be described below with reference to FIG. 8. For convenience purposes, in the flowing description, three samples (pulverized coals A to C) are prepared, and an analysis condition of the simpler analyzer is adjusted based on an analysis result of the samples (pulverized coals A to C). However, the number of samples and the like are not limited to this example.

First, industrial analysis values (moisture content, volatile content, fixed carbon content, ash content) obtained by a high-accuracy industrial analysis method are acquired with respect to a plurality of samples, and a reference NOx estimation value is calculated by substituting the acquired industrial analysis values obtained by the high-accuracy industrial analysis method and the like into a NOx estimating equation (SB1). Subsequently, a plurality of varied NOx estimation values are calculated by varying a value of each of components of the industrial analysis values obtained by the high-accuracy industrial analysis method in a predetermined range, and substituting the varied value into the NOx estimating equation (SB2). Subsequently, each NOx error, which is an error of each varied NOx estimation value with respect to the reference NOx estimation value, is calculated (SB3).

Then, a reference unburned combustible estimation value is calculated by substituting the industrial analysis values obtained by the high-accuracy industrial analysis method and the like into an unburned combustible estimating equation (SB4). Subsequently, in a similar way to the above described step SB2, a plurality of varied unburned combustible estimation values are calculated by varying a value of each of components of the industrial analysis values obtained by the high-accuracy industrial analysis method in a predetermined range, and substituting the varied value into the unburned combustible estimating equation (SB5). Subsequently, each unburned combustible error, which is an error of each varied unburned combustible estimation value with respect to the reference unburned combustible estimation value, is calculated (SB6).

Then, an analysis error tolerance range for each component is set based on the NOx error calculated in step SB3 and the unburned combustible error calculated in step SB6 (SB7).

Then, simple analysis result of the samples (pulverized coals A, B, C) by the simple analyzer is acquired (SB8), and an analysis error for each component is calculated based on the analysis result by the simple analyzer and the analysis result by the high-accuracy industrial analysis method (SB9).

Subsequently, whether or not the analysis error is within the analysis error tolerance range for each component set by in step SB7 (SB10). If it is determined that the analysis error for each component is within the analysis error tolerance range as a result (SB10: YES), then it is determined that the analysis condition of the simple analyzer is appropriate, and notification of such a result is provided (SB11), and this process is terminated. On the other hand, if an analysis error of at least one component is outside the analysis error tolerance range in step SB10, the analysis condition of the simple analyzer is assumed to be inappropriate, and the analysis condition is adjusted (SB12), and the control is returned to step SB8.

In step SB8, each sample (pulverized coal A to C) is reanalyzed by the simple analyzer with the adjusted analysis condition. Then, the following processing is performed using its analysis result. In this way, until the analysis error for each component between the analysis result by the simple analyzer and the analysis result by the high-accuracy industrial analysis method becomes within the analysis error tolerance range, adjustment of the analysis condition of the simple analyzer is repeatedly performed.

Then, if the analysis error for every component is within the analysis error tolerance range (SB10: YES), the control proceeds to step SB11 and provides notification that the analysis result is appropriate, and this process is terminated.

The simple analyzer with an analysis condition adjusted appropriately and with a certain analysis accuracy guaranteed in this manner will be used as an on-site fuel analyzer for analyzing fuel of the boiler 10 as described above. Accordingly, in the combustion adjusting process of the boiler 10 shown in FIG. 6, industrial analysis of fuel to be supplied to the boiler 10 is performed by the simple analyzer, and the analysis result of this simple analyzer is substituted as fuel information into a NOx estimating equation and an unburned combustible estimating equation so that a NOx estimation value and an unburned combustible estimation value are calculated.

As described above, the simple fuel analyzer 25 and the analysis condition adjusting device 60 thereof according to one embodiment of the present invention determines an analysis error tolerance range for keeping the estimation error of NOx estimation value and the estimation error of unburned combustible estimation value to be within a tolerance range, and keeps the analysis error between an industrial analysis result by the high-accuracy industrial analysis method and an analysis result by the simple fuel analyzer to be within an analysis error tolerance range. Therefore, the estimation error of the NOx estimation value estimated using the analysis result of the simple fuel analyzer can be made to be within its tolerance range. Thereby, it is possible to reduce the risk of prolonging the time taken for combustion adjustment, for example.

The simple fuel analyzer 25 can complete fuel analysis in a shorter time than the high-accuracy industrial analysis method, and therefore can perform industrial analysis of fuel to be input to the boiler on site. Thereby, it is possible to perform industrial analysis of fuel to be input to the boiler actually, and eliminate a conventional inconvenience that fuel used in analysis and actual fuel input to the boiler 10 are different in property or the like.

Although the present invention has been described above using the embodiments, the technical scope of the present invention is not limited to the scope of the description of the above embodiments. Various alterations and modifications can be made to the above embodiments without departing from the spirit and scope of the invention, and such altered or improved forms are also included in the technical scope of the present invention. The above embodiments may be combined as appropriate.

One example is flows of the combustion adjusting process and analysis condition adjusting process illustrated in the above embodiments, and an unnecessary step may be removed, a new step may be added, or processing order may be changed without departing from the spirit and scope of the present invention.

For example, although in the above embodiments, an analysis error tolerance range is determined such that both NOx and unburned combustible contents are under or equal to a specified value, the present invention is not limited thereto, for example, an analysis error tolerance range may be determined based only on NOx or unburned combustible.

Although in the above embodiments, in the combustion adjusting process by controller 50, a NOx estimation value and an unburned combustible estimation value are computed using an industrial analysis value or the like of fuel, an elemental analysis value may be additionally used to compute a NOx estimation value and an unburned combustible estimation value. The elemental analysis method to be used may be a combustion method (improved Dumas method) which measures the content of a component based on thermal conductivity of exhaust gas when fuel is burned, or a method which causes reaction with a certain gas using catalyst, detects emission intensity upon reaction with ozone or using infrared absorption method, and identifies the content of component. These analysis methods can obtain analysis result in several minutes or so, therefore allowing on-site analysis. By additionally using an elemental analysis value, the estimation accuracy of NOx and unburned combustible contents can be further improved.

REFERENCE SIGNS LIST

10 Boiler
11 Furnace
12 Burner section
14 AA section
15 Additional air injection nozzle
16 Pulverized coal mixture gas transport pipe
17 Air supply duct
18 Exhaust gas flow path
20 Pulverized coal burner
21 Fuel burner
22 Primary port
23 Secondary port
25 Simple fuel analyzer
30 Port
35 Unburned combustible measuring instrument
37 NOx measuring instrument
40 Damper
50 Controller
51 Information acquiring unit
52 NOx estimating unit
53 Unburned combustible estimating unit
54 Combustion adjusting unit
60 Analysis condition adjusting device
61 First NOx computing unit
62 Second NOx computing unit
63 NOx error computing unit
64 First unburned combustible computing unit
65 Second unburned combustible computing unit
66 Unburned combustible error computing unit
67 Analysis error tolerance range setting unit
68 Analysis error computing unit
69 Determining unit
70 Analysis condition adjusting unit

The invention claimed is:

1. An analysis condition adjusting device of a fuel analyzer comprising:
   a first NOx computing unit for calculating a NOx estimation value as a reference NOx estimation value by inputting a previously obtained first industrial analysis value of a fuel sample into a NOx estimating equation for estimating an amount of NOx in exhaust gas;
   a second NOx computing unit for calculating a plurality of varied NOx estimation values by varying a value of each of components of the first industrial analysis value and inputting the varied value of each component into the NOx estimating equation;
   a NOx error computing unit for computing an error of each of the varied NOx estimation values relative to the reference NOx estimation value, as a NOx error;
   an analysis error tolerance range setting unit for determining a value variation amount of each of the components such that the NOx error is within a tolerance range, and setting an analysis error tolerance range of each of the components based on the determined value variation amount;
   an analysis error computing unit for computing, for each component, an analysis error between a value of each of components of a second industrial analysis value of the fuel sample analyzed by the fuel analyzer and the value of each component of the first industrial analysis value;
   a determining unit for determining whether or not the analysis error for each component is within the analysis error tolerance range set for each component; and
   an analysis condition adjusting unit for adjusting an analysis condition of the fuel analyzer until the analysis error for each component becomes within the analysis error tolerance range set for each component.

2. The analysis condition adjusting device according to claim 1, comprising:
   a first unburned combustible computing unit for calculating an unburned combustible estimation value as a reference unburned combustible estimation value by inputting the previously obtained first industrial analysis value of the fuel sample into an unburned combustible estimating equation for estimating an amount of unburned combustible in exhaust gas;
   a second unburned combustible computing unit for calculating a plurality of varied unburned combustible estimation values by varying a value of each of the components of the first industrial analysis value and inputting the varied value of each component into the unburned combustible estimating equation; and
   an unburned combustible error computing unit for computing an error of each of the varied unburned combustible estimation values relative to the reference unburned combustible estimation value, as an unburned combustible error,
   wherein the analysis error tolerance range setting unit determines a value variation amount of each of the components such that the NOx error and the unburned combustible error are within their tolerance ranges, and setting an analysis error tolerance range of each of the components based on the determined value variation amount.

3. A fuel analyzer, comprising: the analysis condition adjusting device according to claim 1, wherein an analysis condition of the fuel analyzer is adjusted using the analysis condition adjusting device.

4. A controller for controlling a boiler, the controller comprising: the fuel analyzer according to claim 3 for analyzing a fuel supplied to the boiler;
   a NOx estimating unit for estimating an amount of NOx in exhaust gas to be exhausted from the boiler, by using in a NOx estimating equation an analysis result obtained by the fuel analyzer;
   an unburned combustible estimating unit for estimating an amount of unburned combustible in the exhaust gas to be exhausted from the boiler, by using in an unburned combustible estimating equation the analysis result obtained by the fuel analyzer; and a combustion adjusting unit for controlling an operation end for adjusting a combustion state of the boiler, such that the amount of NOx estimated by the NOx estimating unit and the amount of unburned combustible estimated by the unburned combustible estimating unit are within their tolerance ranges.

5. An analysis condition adjusting device of a fuel analyzer comprising:
a first unburned combustible computing unit for calculating an unburned combustible estimation value as a reference unburned combustible estimation value by inputting a previously obtained first industrial analysis value of a fuel sample into an unburned combustible estimating equation for estimating an amount of unburned combustible in exhaust gas;
a second unburned combustible computing unit for calculating a plurality of varied unburned combustible estimation values by varying a value of each of components of the first industrial analysis value and inputting the varied value of each component into the unburned combustible estimating equation;
an unburned combustible error computing unit for computing an error of each of the varied unburned combustible estimation values relative to the reference unburned combustible estimation value, as an unburned combustible error;
an analysis error tolerance range setting unit for determining a value variation amount of each of the components such that the unburned combustible error is within a tolerance range, and setting an analysis error tolerance range of each of the components based on the determined value variation amount;
an analysis error computing unit tor computing, for each component, an analysis error between a value, of each of components of a second industrial analysis value of the fuel sample analyzed by the fuel analyzer and the value of each component of the first industrial analysis value;
a determining unit for determining whether or not the analysis error for each component is within the analysis error tolerance range set tor each component and an analysis condition adjusting unit for adjusting an analysis condition of the fuel analyzer until the analysis error for each component becomes within the analysis error tolerance range set for each component.

6. A method for adjusting an analysis condition of a fuel analyzer, the method comprising:
a first NOx computing step of calculating a NOx estimation value as a reference NOx estimation value by inputting a previously obtained first industrial analysis value of a fuel sample into a NOx estimating equation for estimating an amount of NOx in exhaust gas;
a second NOx computing step of calculating a plurality of varied NOx estimation values by varying a value of each of components of the first industrial analysis value and inputting the varied value of each component into the NOx estimating equation,
a NOx error computing step of computing an error of each of the varied NOx estimation values relative to the reference NOx estimation value, as a NOx error;
an analysis error tolerance range setting step of determining a value variation amount of each of the components such that the NOx error is within a tolerance range, and setting an analysis error tolerance range of each of the components based on the determined value variation amount; an analysis error computing step of computing, for each component,
an analysis error between a value of each of components of a second industrial analysis value of the fuel sample analyzed by the fuel analyzer and the value of each component of the first industrial analysis value;
a determining step of determining whether or not the analysis error for each component is within the analysis error tolerance range set for each component; and
an analysis condition adjusting step of adjusting the analysis condition of the fuel analyzer until the analysis error for each component becomes within the analysis error tolerance range set for each component.

7. A method for adjusting an analysis condition of a fuel analyzer, the method comprising:
a first unburned combustible computing step of calculating an unburned combustible estimation value as a reference unburned combustible estimation value by inputting a previously obtained first industrial analysis value of a fuel sample into an unburned combustible estimating equation for estimating an amount of unburned combustible in exhaust gas;
a second unburned combustible computing step of calculating a plurality of varied unburned combustible estimation values by varying a value of each of components of the first industrial analysis value and inputting the varied value of each component into the unburned combustible estimating equation;
an unburned combustible error computing step of computing an error of each of the varied unburned combustible estimation values relative to the reference unburned combustible estimation value, as an unburned combustible error;
an analysis error tolerance range setting step of determining a value variation amount of each of the components such that the unburned combustible error is within a tolerance range, and setting an analysis error tolerance range of each of the components based on the determined value variation amount;
an analysis error computing step of computing, for each component, an analysis error between a value of each of components of a second industrial analysis value of the fuel sample analyzed by the fuel analyzer and the value of each component of the first industrial analysis value;
a determining step of determining whether or not the analysis error for each component is within the analysis error tolerance range set for each component; and
an analysis condition adjusting step of adjusting the analysis condition of the fuel analyzer until the analysis error for each component becomes within the analysis error tolerance range set for each component.

* * * * *